(12) United States Patent
Verbraak et al.

(10) Patent No.: US 7,814,774 B2
(45) Date of Patent: Oct. 19, 2010

(54) METHOD AND APPARATUS FOR EVALUATION OF A DEVICE FOR MEASURING LUNG DIFFUSION CAPACITY

(75) Inventors: Antonius Fransiscus Marie Verbraak, Dordrecht (NL); Wilhelmus Petrus Johannes Holland, Rotterdam (NL)

(73) Assignee: Erasmus University Medical Center Rotterdam (NL)

( * ) Notice: Subject to any disclaimer, the term of this patent is extended or adjusted under 35 U.S.C. 154(b) by 3 days.

(21) Appl. No.: 12/095,769

(22) PCT Filed: Mar. 27, 2006

(86) PCT No.: PCT/NL2006/000157

§ 371 (c)(1),
(2), (4) Date: Oct. 13, 2008

(87) PCT Pub. No.: WO2007/111494

PCT Pub. Date: Oct. 4, 2007

(65) Prior Publication Data

US 2009/0038371 A1    Feb. 12, 2009

(51) Int. Cl.
*G01N 21/00* (2006.01)

(52) U.S. Cl. .................................................. 73/1.06

(58) Field of Classification Search .................. None
See application file for complete search history.

(56) References Cited

U.S. PATENT DOCUMENTS

| 2,068,882 | A | * | 1/1937 | Walker ........................ 423/176 |
| 5,193,551 | A | * | 3/1993 | Pilipski ....................... 600/529 |
| 5,303,712 | A | | 4/1994 | Van Duren |
| 5,596,129 | A | * | 1/1997 | Murashige et al. .......... 562/414 |
| 6,415,642 | B1 | | 7/2002 | Crapo et al. |

FOREIGN PATENT DOCUMENTS

| EP | 1109018 | 6/2001 |
| WO | 00/72754 | 12/2000 |

* cited by examiner

*Primary Examiner*—Robert R Raevis
(74) *Attorney, Agent, or Firm*—The Webb Law Firm

(57) ABSTRACT

A method of evaluating a measuring device for measuring, in normal operation, a diffusion capacity of a person's lungs by measuring a change of concentration of a gas species in a mixture, when the mixture is inhaled and subsequently exhaled by the person or imposed by an artificial ventilator, the method comprising the steps of: (a) receiving the mixture in a compartment; (b) circulating gas from the compartment back to the compartment through a circulation circuit; and (c) selectively reducing partial pressure of the gas species in the circulation circuit to a predetermined level. A device for implementing the evaluation method is also disclosed.

8 Claims, 2 Drawing Sheets

METHOD AND APPARATUS FOR EVALUATION OF A DEVICE FOR MEASURING LUNG DIFFUSION CAPACITY

FIELD OF THE INVENTION

The invention relates to a method and apparatus for evaluating an apparatus for measuring a diffusion capacity of a person's lungs.

BACKGROUND OF THE INVENTION

U.S. Pat. Nos. 5,193,551 and 6,415,642 B1 describe a method and apparatus for calibrating an apparatus for measuring a diffusion capacity of a person's lungs.

Apparatuses for measuring a diffusion capacity of a person's lungs are known per se. In particular Oxygen diffusion is an important clinical measure. The rate of Oxygen diffusion from the lungs to the blood depends on diffusion capacity, and the difference between the Oxygen pressure in the blood and the alveolar space of the lungs. In clinical laboratories, lung diffusion capacity is usually measured for carbon monoxide (CO) instead of Oxygen. The reason is the very high affinity of CO for hemoglobine, which helps to keep the CO pressure in the capillary blood negligible small compared to the CO pressure in the alveolar space. Consequently, unlike the O2 diffusion capacity, the CO diffusion capacity (DLCO) can be determined non-invasively, because the pressure in the blood does not need to be measured. This is an important advantage in clinical routine. The membrane diffusion capacities $DLO_2$ and DLCO appear to have comparable diagnostic values. Therefore, the use of CO as a test gas for measuring diffusion capacity has become standard clinical practice.

Various measurement techniques exist to measure DLCO, such as single breath, multiple breath, re-breathing and steady state methods. For many decades, the single breath (SB) technique has become the technique of choice in nearly all lung function departments and laboratories all over the word. SB machines are commercially available from several manufacturers. Good medical practice requires that these machines have to be maintained and kept in good conditions. So there is a strong need for proper devices to evaluate the machines, in an easy and uncomplicated manner (As used herein "evaluation" is any process that results in information about the operation of the DLCO measuring apparatus. Calibrating and testing are examples of "evaluating" as used herein).

Typically the procedure of a DLCO measurement with a SB machine is as follows. A person connected to the SB machine is ordered first to expire maximally so that a residual volume (V0, initial volume) remains in the lung, then immediate afterwards to inhale maximally. At the end of the volume inhaled (VI) the patient keeps his breath during a certain breath hold time (BHT). The lung volume at breath hold time is V0+VI. The breath hold time can be for example 10 seconds. During the inhalation phase the SB machine provides a gas mixture containing test gas components which the patient inhales into his lungs; the test gas components are CO and an inert reference gas (inert gas, IG) like He, Ne, or CH4, both with known, pre-adjusted, concentrations.

Once the patient has inhaled the gas mixture, the inertgas will be diluted by the residual volume of air mixture in the lungs that remains in the lungs all the time, while the CO, after dilution like the inert gas, and after diffusing to the bloodstream, is carried away by the bloodstream. Thus, in the lungs, the relative decrease of CO is greater then that of the inert gas IG. After the breath hold time the patient exhales, an alveolar sample of the exhaled gas is collected by the SB-machine where it is analysed for CO—and inert gas concentration.

This results in the quantitative measurements of diffusion capacity using the following considerations. Quantities VI, BHT, rCO and rIG are measured. rIG is the ratio of measurements of exhalation and inhalation concentration of the inert gas IG. rCO is the ratio of measurements of those concentrations of CO. VI is the inhaled/exhaled volume and BHT is the breath hold time. The condition for diffusion in the lung can then be stated as rCO<rIG<1. During the breath hold time CO disappears through diffusion through the membrane, and as a result its concentration decreases in time. Assuming that the lung consists of one single alveolar compartment, this decrease has an exponential shape because the disappearance rate is proportional to the concentration gradient across the membrane, and this is changing continuously.

DLCO is obtained from the measurement data as $$DLCO = -1/(R*T)*\ln(rCO/rIG)/BHT*VI/rIG \quad (1)$$

where R is the gas constant and T is absolute temperature in the lung (for example 310 K), and "ln" refers to the Naperian logarithm.

Unfortunately the apparatus for measuring DLCO can malfunction, which can lead to erroneous DLCO results, for example when the determination of CO concentration, IG concentration or the volume VI suffered from errors. Therefore reliable computation of DLCO requires evaluating of the apparatus for measuring DLCO that uses the SB technique, to verify that it produces the correct results. U.S. Pat. Nos. 5,193,551 and 6,415,642 describe this type of evaluating. Both devices uses a large-volume syringe (gas cylinder with piston) to simulate the volume and volume changes of the lungs. The mouth of the syringe is connected to the mouth connection of the SB apparatus under evaluation. The volume of the internal syringe space is changed manually by a technician in the same sequence as for the SB technique (as described above), including an inhalation phase, a breath holding phase, and an exhalation phase. Both these devices intentionally modify the concentrations of inert gas and CO in the exhaled gas mixture; in such a manner that the resulting concentrations satisfy the above-mentioned conditions for CO-diffusion.

U.S. Pat. No. 5,193,551 describes a calibration device using a syringe that is connected via a special purpose inter-space chamber with the SB-test machine. On some time before, a certain amount of the used inert gas is brought into the inter-space chamber. During the inhalation phase the gas mixture supplied by the machine (containing CO and inert gas) flows through the inter-space chamber into the syringe volume space, thereby taking up some of the inert gas initially present in the inter-space chamber. So, besides the volumetric dilution of the CO and inert gas, the inert gas is subjected to an additional increase. During the exhalation phase the gas in the syringe space is returned directly, without streaming through the inter-space chamber, to the evaluation machine. The resulting exhaled/inhaled concentration ratios then satisfy the condition rCO<rIG<1, signifying that CO-diffusion has validly been simulated. After analysis and subsequent calculations in the evaluation machine using a similar formula as equation (1), a DLCO-value can be predicted.

A critical point of this device is the precise prediction of the fractional reduction ratios rIG and rCO. These ratios depend on the precise amount of dilution in the inter-space chamber, which in turn will depend on the particular state of gas flow and convection in the inter-space chamber (be it plug flow, ideal mixing, or some intermediate state between). However, the document supplies no information how to predict these ratios from the dilution process. Assuming that the dilution process in the inner-space chamber behaves reproducibly, the resulting simulated DLCO value will be reproducible as well, which would make this device still useful as a relative DLCO calibrator.

U.S. Pat. No. 6,415,642 describes a calibration device using two syringes. The SB machine under evaluation is connected with the first syringe with which the inhalation phase is simulated. A short time before the start of the exhalation phase the other syringe is connected to the evaluation-machine. This second syringe has been filled with a test gas mixture containing CO and inert gas with precisely known concentrations that are carefully chosen so as to satisfy the condition rCO<rIG<1. In that case the SB machine can produces valid simulated DLCO values, useful for test- and calibration purposes.

In both patents the obtained DLCO-value depends on several parameters: the supplied inhaled volume, the CO and inert gas concentration in the machine gas mixture as well as in the required precision test gas mixture. This makes calibration complex and sensitive to errors in these parameters. Moreover, these calibrators can only be used for testing SB-equipment.

SUMMARY OF THE INVENTION

Among others it is an object of the invention to provide for easier and/or more accurate evaluation of a diffusion measuring apparatus.

A method and apparatus are provided according to the independent claims. A compartment is provided for receiving a gas mixture from the diffusion measuring apparatus. Gas from the compartment circulates from the compartment back to the compartment through a circulation circuit. Partial pressure of a gas species like CO is selectively reduced to a predetermined level in the circulation circuit (e.g. substantially to zero). Thus an accurate quantitative simulation of diffusion can be realized independent of other parameters by controlling the rate of flow through the circulation circuit.

BRIEF DESCRIPTION OF THE DRAWINGS

These and other objects and advantages will become apparent from the following description of exemplary embodiments, using the following figures.

DETAILED DESCRIPTION OF THE INVENTION

Figure 1:
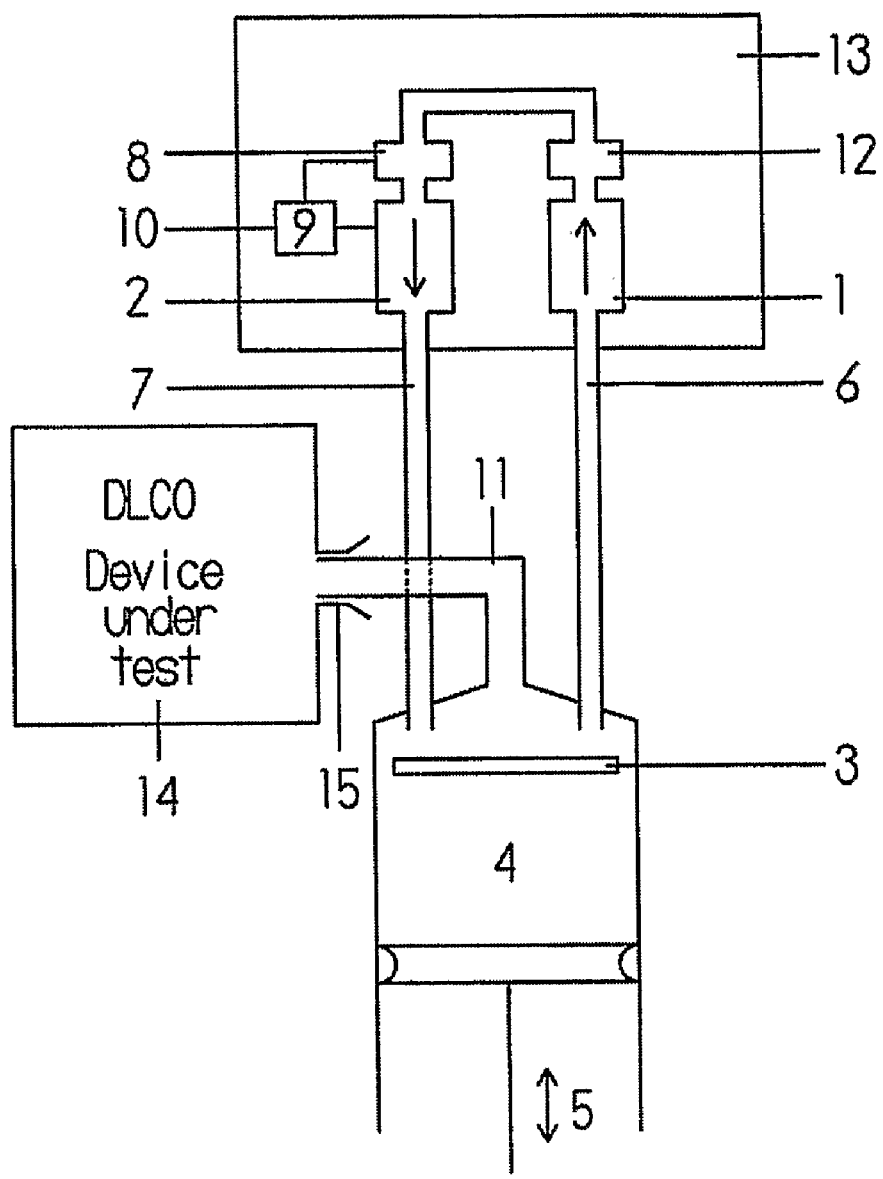
FIG. 1 schematically shows a high-end evaluation apparatus.

FIG. 1 schematically shows a high-end evaluation apparatus CO-TS. The CO-TS (CO-Transfer Simulator) comprises a compartment 4 coupled to a conditioning unit 13 via an input connection tube 6 and an output connection tube 7. Conditioning unit 13 comprise a canister 1, a sensor 12, a pump 2, a flow transducer 8 and a flow controller 9. Canister 1, sensor 12, flow transducer 8 and pump 2 are coupled in series between input connection tube 6 and an output connection tube 7. Canister 1 contains a material that dries the gas (if necessary) and eliminates all the CO from the gas flowing through canister 1. The CO removing material may be Moleculite™ 403 for example and the drying material may be calcium chloride for example.

In operation a gas-flow is sucked out of compartment 4 through connection tube 6. This gas-flow is led through a canister 1 where the gas is dried (if necessary) and substantially all CO from the gas is eliminated (e.g. to less than 2% of its original partial pressure).

The gas passes to CO-sensor 12, which is optionally provided to measure concentration of CO-gas still remaining in the gas coming out of canister 1. The sensor only functions to test the effectiveness of the material in canister 1. When the CO-TS is functioning properly the concentration value of CO should be substantially zero. If not the material in canister 1 has lost its effectiveness after some time, this is indicated by sensor 12, so that the material can be replaced.

Pump 2 provides flow through conditioning unit 13. This flow is measured by means of a flow transducer 8. The measured flow is used as input for flow controller 9. Flow controller regulates the flow of pump 2 to a pre-set value. A control input 10 may be provided to set this value by hand or by means of software in a control computer (not shown). From pump 2, the gas is led back into the compartment 4 through output connection tube 7. Inside compartment 4 a fan 3 is provided to ensure of a proper mixing of the gas inside compartment 4.

An embodiment is shown wherein the compartment 4 is of type of which the volume can be changed. In the example shown in the figure, the volume can be changed by means of a servo-controlled piston, but alternatively compartment 4 may be partly or completely in the form of a bellows. The use of a compartment 4 with adjustable volume simulates breathing in and breathing out. In an embodiment a control computer (not shown) is provided to control the change of volume as a function of time. A sinusoidal volume cycle may be used for example, or any other volume as a function of time. By using a computer controlled patterns of changes these patterns of changes can be repeated accurately. The change of volume (indicated by arrows 5) can also be performed by hand if the quality of the desired pattern is less important. Trough a port 11 the CO-TS is connected to the device under evaluation 14.

A control computer (not shown) may be configured to control the flow through the canister in relation to the value of the volume space in order to mimic the dependency of DLCO of alveolar volume. If necessary flow controller 9 can be integrated in the control computer. The apparatus of FIG. 1 simulates a CO diffusion capacity of the lung that is equal to the flow rate realized by pump 2. The simulated DLCO equals $V'/(R*T)$, wherein V' is the flow rate, R is the gas constant and T is absolute temperature. With flow rates of 3-30 liters per minute DLCO's from those for babies to those of athletes can be simulated. The DLCO value can be set by setting flow rate, which makes it easy to calibrate DLCO measurements of the measurement apparatus for different DLCO values. There is no effect of inhalation and residue volumes and no reference gas supply is needed.

It should be appreciated that this form of simulation enables reliable evaluation of all types of CO diffusion measurement, including not only single breath measurement, but also the known multiple breath measurements, re-breathing and steady state methods to be used on patients breathing themselves or artificially ventilated. Preferably, a plurality of measurements is performed at different flow rates to obtain verification of the measurement for different diffusion capacity values. This can be realized by adjusting the flow rate in different measurements, using flow controller 9.

In general, diffusion capacity in the natural lung increases when the volume of the lung increases, because lung surface area increases. Therefore, it may be desirable to simulate a normalized diffusion capacity, which corresponds to a defined pattern of variation of diffusion capacity in correlation with volume of the lung. Simulation of measurements of such a normalized diffusion capacity can be realized by making flow controller 9 increase the flow rate when the volume of compartment 4 increases and vice versa. At each point in time a flow rate that is a predetermined function (e.g. a linear function) of the volume at that point of time may be set for example. Alternatively, both the volume changes and the flow rate may be controlled as predetermined functions of time. In this way, a more accurate evaluation of measurements of normalized diffusion capacity under natural breathing circumstances can be realized.

Figure 2:
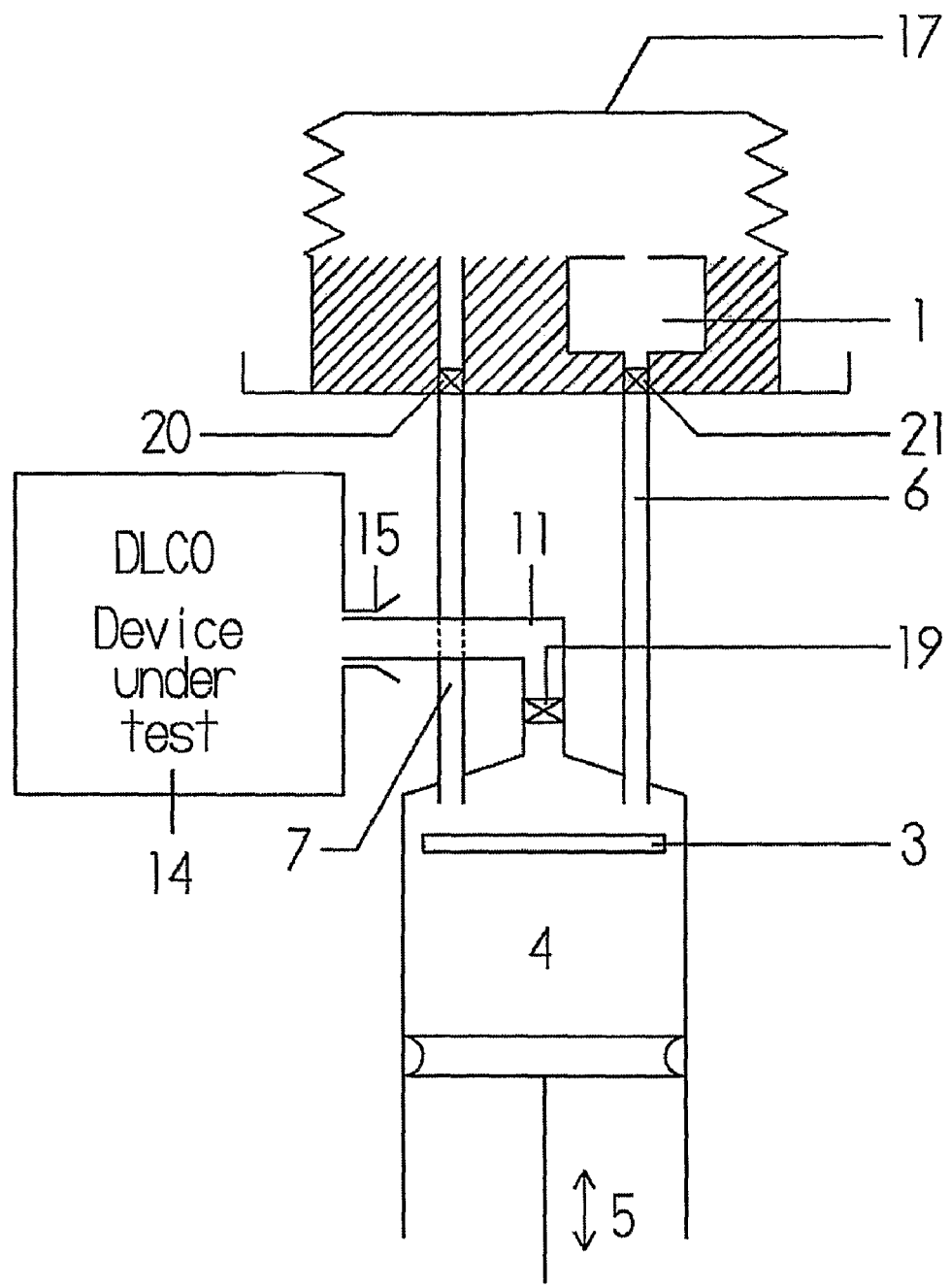
FIG. 2 shows a low-end evaluation apparatus

FIG. 2 shows a low-end solution for use in testing a Single-Breath (SB) measurement device. The normal procedure for the SB-measurement is as follows: a patient breaths normally (phase I), and subsequently a technician ask the patient to take a deep breath in until Total Lung Capacity is reached (phase II). Thereafter during 10 seconds the breath is held (phase III), after which an expiration follows (phase IV).

In this case a much simpler embodiment of the CO-TS can be used. The basics of this CO-TS are the same but a much simpler conditioning is used. In this set-up there are a first, second and third valve 19, 20, 21. The compartment 4 with piston can be connected to the device under test, output connection tube 7 or input connection tube 6 via first valve 19, second valve 20 and third valve 21, respectively. In most situations valve 19 is already incorporated in the device under test.

During phase I and phase II, the volume is connected to the device under test (first valve 19 open and second and third valves 20 and 21 closed). At the end of a simulated deep breath-in, first valve 19 is closed and third valve 21 is opened. Then a predefined amount of gas is squeezed out of the compartment 4, through the canister 1 into the volume space inside a bellows 17 by moving the piston in (Phase III-a). Thereafter, the third valve 21 is closed and second valve 20 is opened, and the same amount of air is sucked out from the space inside bellows 17 back into the volume space (number 4) by pulling the piston with the same amount (phase III-b). Then again second valve 20 is closed. Thereafter first valve 19 is opened, where after expiration follows (phase IV). This procedure must be performed within the time-window between closing and opening of first valve 19, e.g., by performing phases IIIa an IIIb during ten seconds, which corresponds to the duration that the air remains breathed in a SB experiment. The amount of gas that is led through the canister is again a measure for the DLCO. The inner volume of gas space of the cannister 1 and the connecting tubes 6 and 7 is preferably as small as possible. The volume of space inside bellows 17 is constructed such that it is as low as possible before Phase III-a is started. First valve 19 will be under control of the device under test. Second and third valves 20 and 21 can be one-way valves that open in response to a small pressure differential in one direction.

In the embodiment of FIG. 2 the simulated DLCO value depends on the volumes of compartment 4 and bellows 17. If the initial volume of compartment 4 equals V0 and the volume with simulated inhaled air V1 (=V0+VI). The volume change of bellows 17 is designated by VP. In this case the CO concentration in exhaled air is reduced by a factor $rCO=VI/V1*(V1-VP)/V1$ and the inert gas concentration is reduced by a factor $rIG=VI/V1$. These factors are substituted in eq (1) of the SB-method. Hence the simulated DLCO value is $$DCLO=-1/(R*T)*\ln(1-VP/V1)/BHT*V1 \quad \text{eq(2)}$$

Different DLCO values can be set by selecting different values of V1 and VP, for example by varying the extent to which bellows 17 is extended, or by selecting the initial position of the piston.

As will be appreciated the results of the measurements of both apparatus can be used to decide whether the apparatus functions properly.

In a further embodiment the results of such evaluation measurements can be compiled into a calibration factor or a calibration table to calibrate operating parameters of the apparatus for measuring DLCO. For example, output signals of a gas analyser in the apparatus for measuring DLCO could be calibrated directly, or as part of the overall apparatus for measuring DLCO, by determining calibration values that are needed to obtain a predicted DLCO value given a simulated diffusion capacity value realized with a flow rate used during calibration. This may be repeated for different flow rates in order to obtain a calibration table in the case of a non-linear response; but in some cases a single measurement may suffice to define a calibration factor.

Such calibration data may be programmed into the DLCO measurement apparatus for conversion of measurement results during subsequent use with one or more persons, for example during a predetermined time period (such as a day or a week). Alternatively, a written table for use by an operator may be generated for example.

In a further embodiment calibration data may be gathered for a variety of breathing conditions, so that breathing condition dependent corrections to computed DLCO values can be provided. In this way, no conditions need to be imposed on the way of breathing of the person under investigation. Thus for example, measurements are possible on a person that is unconscious or otherwise incapable of following instructions.

In a further alternative, the calibration may be performed for a single person at a time, the pattern of volume changes, setting flow rates, flow rate changes in correlation volume changes etc. until they correspond to those of the person under investigation.

The invention claimed is:

1. A method of evaluating a measuring device for measuring, in normal operation, a diffusion capacity of a person's lungs by measuring a change of concentration of a gas species in a mixture, when the mixture is inhaled and subsequently exhaled by the person or imposed by an artificial ventilator, the method comprising the steps of:
   (a) receiving the mixture in a compartment;
   (b) circulating gas from the compartment back to the compartment through a circulation circuit; and
   (c) selectively reducing partial pressure of the gas species in the circulation circuit to a predetermined level.

2. The method of evaluating the measuring device according to claim 1, further comprising the step of regulating a flow of the circulating gas to a set flow rate.

3. The method of evaluating the measuring device according to claim 2, further comprising the step of force-mixing of the mixture in the compartment.

4. The method of evaluating the measuring device according to claim 1, wherein the predetermined level substantially corresponds to zero partial pressure.

5. The method of evaluating the measuring device according to claim 1, wherein the gas species is carbon monoxide.

6. The method of evaluating the measuring device according to claim 1, further comprising the step of changing the volume of the compartment as a function of time during a measurement cycle, and varying a controlled flow rate of the flow of the circulating gas in correlation with the changes of the volume during the measurement cycle.

7. The method of evaluating the measuring device according to claim 1, further comprising the step of generating a calibration as a function of diffusion capacity, by performing a series of calibration cycles, each including the receiving step (a), the circulating step (b) and the reducing step (c), and further comprising the step of controlling a flow during the circulating step (b) to respective flow rates in respective flow rates of the calibration cycles.

8. A test apparatus for evaluating a measuring device for measuring a diffusion capacity of a person's lungs by measuring a change of concentration of a gas species in a mixture, when the mixture is inhaled and subsequently exhaled by a person, the test apparatus comprising:

means for receiving the mixture in a compartment;

means for circulating gas from the compartment back to the compartment through a circulation circuit; and means for selectively reducing partial pressure of the gas species in the circulation circuit to a predetermined level.

\* \* \* \* \*

UNITED STATES PATENT AND TRADEMARK OFFICE
CERTIFICATE OF CORRECTION

| | | |
|---|---|---|
| PATENT NO. | : 7,814,774 B2 | Page 1 of 1 |
| APPLICATION NO. | : 12/095769 | |
| DATED | : October 19, 2010 | |
| INVENTOR(S) | : Verbraak et al. | |

It is certified that error appears in the above-identified patent and that said Letters Patent is hereby corrected as shown below:

Title Page, See Item (86), PCT information, line 3, "Oct. 13, 2008" should read --Oct. 3, 2008--

Signed and Sealed this
First Day of March, 2011

David J. Kappos
*Director of the United States Patent and Trademark Office*